(12) United States Patent
Shortt

(10) Patent No.: US 6,948,223 B2
(45) Date of Patent: Sep. 27, 2005

(54) APPARATUS FOR MOUNTING A STENT ONTO A STENT DELIVERY SYSTEM

(75) Inventor: James Shortt, Co. Meath (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 10 days.

(21) Appl. No.: 10/137,886

(22) Filed: May 3, 2002

(65) Prior Publication Data

US 2003/0208254 A1 Nov. 6, 2003

(51) Int. Cl.[7] .............................................. B25B 27/14
(52) U.S. Cl. .......................... 29/272; 29/282; 29/447; 623/1.11; 72/416; 264/345
(58) Field of Search .......................... 29/447, 516, 517, 29/235, 272, 282; 72/416; 623/1.11; 264/342 R, 345, 904

(56) References Cited

U.S. PATENT DOCUMENTS

| 5,759,474 A | * | 6/1998 | Rupp et al. ................. 264/496 |
| 5,836,965 A | | 11/1998 | Jendersee et al. |
| 5,951,540 A | * | 9/1999 | Verbeek ........................ 606/1 |
| 6,063,092 A | | 5/2000 | Shin |
| 6,159,229 A | | 12/2000 | Jendersee et al. |
| 6,309,402 B1 | | 10/2001 | Jendersee et al. |
| 6,364,870 B1 | * | 4/2002 | Pinchasik ....................... 606/1 |
| 6,481,262 B2 | * | 11/2002 | Ching et al. .................. 72/416 |
| 6,604,403 B1 | * | 8/2003 | Eslambolchi et al. ......... 72/416 |
| 6,612,012 B2 | * | 9/2003 | Mitelberg et al. ............ 29/447 |

FOREIGN PATENT DOCUMENTS

| EP | 1 000 591 A2 | 5/2000 |
| EP | 1 000 593 A2 | 5/2000 |

* cited by examiner

Primary Examiner—Jermie E. Cozart (57) ABSTRACT

The present invention provides a method and apparatus for mounting a stent onto a balloon on a stent delivery system. A stent is then loaded onto the delivery system and the resulting stent/balloon assembly is positioned in a first section of a mould and a second section of the mould is closed onto the first section and locked in place. Pressure is applied to the delivery system through a luer and the mould is heated. The pressure and heat are discontinued and the mould is cooled; this combination of heat and pressure secures the stent to the balloon. The method may include a cooling cycle to help retain the profile of the final stent delivery assembly.

3 Claims, 7 Drawing Sheets

APPARATUS FOR MOUNTING A STENT ONTO A STENT DELIVERY SYSTEM

FIELD OF THE INVENTION

The present invention relates to a method and apparatus for mounting a stent onto a balloon on a stent delivery system.

BACKGROUND OF THE INVENTION

Intraluminal stenting is useful in treating tubular vessels in the body that are narrowed or blocked and it is an alternative to surgical procedures that intend to bypass such an occlusion. When used in endovascular applications, the procedure involves inserting a prosthesis into an artery and expanding it to prevent collapse of the vessel wall.

Percutaneous transluminal angioplasty (PTCA) is used to open coronary arteries, which have been occluded by a build-up of cholesterol fats or atherosclerotic plaque. Typically, a guide catheter is inserted into a major artery in the groin and is passed to the heart, providing a conduit to the ostia of the coronary arteries from outside the body. A balloon catheter and guidewire are advanced through the guiding catheter and steered through the coronary vasculature to the site of therapy. The balloon at the distal end of the catheter is inflated, causing the site of the stenosis to widen. Dilation of the occlusion, however, can form flaps, fissures or dissections, which may threaten re-closure of the dilated vessel. Implantation of a stent can provide support for such flaps and dissections and thereby prevent reclosure of the vessel. Reducing the possibility of restenosis after angioplasty reduces the likelihood that a secondary angioplasty procedure or a surgical bypass operation will be necessary.

A stent is typically a hollow, generally cylindrical device formed from wire(s) or a tube and the stent is commonly intended to act as a permanent prosthesis. A stent is deployed in a body lumen from a radially contracted configuration into a radially expanded configuration, which allows it to contact and support the vessel wall. The stent can be made to be either radially self-expanding or expandable by the use of an expansion device. The self-expanding stent is made from a resilient material while the device-expandable stent is made from a material that is plastically deformable.

A plastically deformable stent can be implanted during an angioplasty procedure by using a balloon catheter bearing the compressed stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally and positioned at a desired location by means of the balloon catheter. A balloon of appropriate size and pressure may be first used to open the lesion. The process can be repeated with a stent loaded onto a balloon. A direct stenting procedure involves simultaneously performing angioplasty and stent implantation using a stent mounted on a dilatation balloon. After the balloon is withdrawn, the stent remains as a scaffold for the injured vessel.

In particular, the present invention relates to stents which can be delivered to a body lumen and which can be deployed at a treatment site by expanding the stent radially from a crimped state into an expanded state in which the stent supports the walls of the vessel at the treatment site. As noted above, the radial expansion is achieved by inflating a balloon on which the stent is located. One problem that can arise with this type of stent delivery system is that the stent may accidentally be displaced on the balloon as the delivery system negotiates torturous body vessels along its path to the treatment site. In order to ensure proper placement of the stent at the treatment site, one must avoid relative movement between the stent and the balloon. One means by which this risk of relative movement between the balloon and stent may be lessened is to form pillows on the balloon on either side of the stent to help prevent the stent from slipping off the balloon. Another means of achieving this object is to securely mount the stent onto the balloon.

Figure 1:
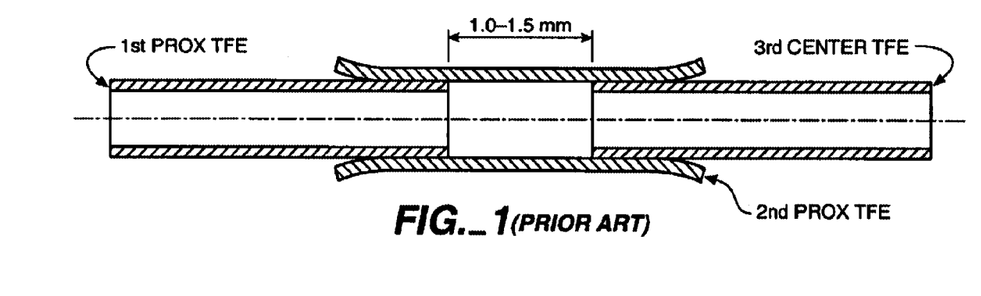
FIG. 1 is a cross-section view showing the prior art method of mounting the stent onto the balloon delivery system using first, second and third TFE sheaths.
Figure 2:
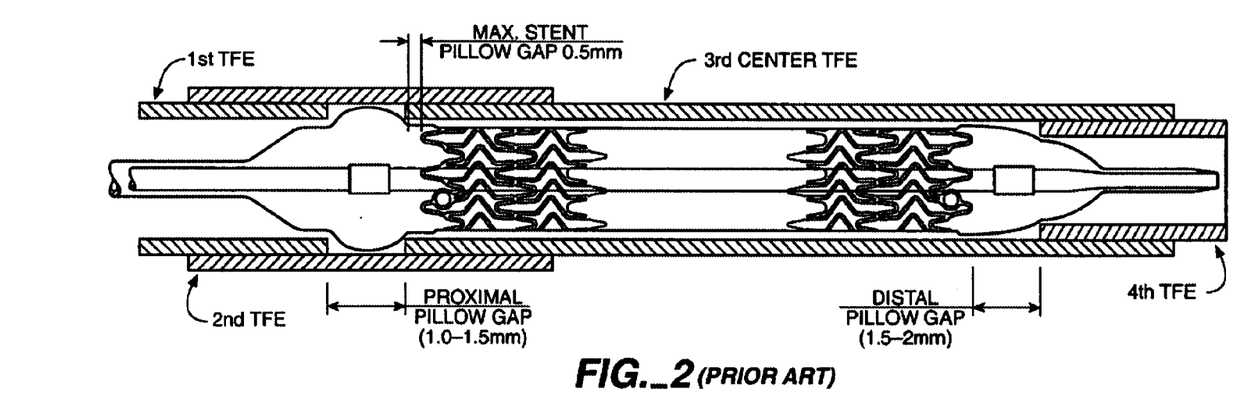
FIG. 2 is a cross-sectional view of the prior art complete assembly.

An existing process for securely mounting the stent uses a series of tetrafluoroethylene (TFE) sheaths positioned over the stent/balloon assembly followed by a heat set operation using hot air and pressure applied to the balloon. The steps involved in this prior art process are as follows. First, the stent is crimped down to the required size. TFE sheaths to be used in the process are cut to length and slits are made in the sheaths to facilitate their removal when the process is complete. First, second and third TFE sheaths 20, 21 and 22 are assembled as shown in FIG. 1 (prior art). This assembly is then loaded onto the delivery system. The stent 23 is loaded onto the delivery system and positioned on the balloon 24 between the markers 25 and 26. The TFE assembly is then positioned carefully over the stent/balloon assembly. This positioning defines the proximal balloon pillow 27. A fourth TFE sheath 28 is then loaded onto the distal end of the assembly and positioned relative to the distal end of the stent. The positioning of this sheath defines the distal balloon pillow 29. The complete assembly is shown in FIG. 2 (prior art). This assembly with the delivery system, stent and TFE sheaths is then loaded into a heat set machine. This machine applies a high pressure to the balloon interior through the delivery system luer fitting so as to push the balloon against the ID (internal diameter) of the stein. The balloon is prevented, by the TFE sheaths, from fully inflating. This assembly, under pressure, is moved into a hot air source so that heating is applied to the stent/balloon assembly. This combination of heat and pressure secures the stent to the balloon. After the heat fix operation, the TFE sheaths are removed from the assembly and discarded. Thus, the process of the prior art is time consuming, wasteful of materials and can be used to manufacture only limited range of design of the final profile.

The present invention seeks to alleviate the disadvantages of the prior art method. The method of the present invention uses a mould in place of the TFE sheaths. This mould is part of a new heat set apparatus, also provided by the present invention.

SUMMARY OF THE INVENTION

Accordingly, the present invention provides a method of mounting a stent onto a balloon on a stent delivery system, the method comprising the following steps. First, the stent is crimped down to the required size. The stent is then loaded onto the delivery system and positioned on the balloon between markers. The stent/balloon assembly is positioned in a first section of a mould and a second section of the mould is closed onto the first section and locked in place. Pressure is applied to the delivery system through a luer and the mould is heated. The pressure and heat are discontinued and the mould is cooled. This combination of heat and pressure secures the stent to the balloon. The method may include a cooling cycle to help retain the profile of the final stent delivery assembly.

Preferably the mould comprises a top half and a bottom half. During the process, the stent/balloon assembly is positioned in the bottom half of the mould and the top half of the mould is closed over onto the bottom half.

Any suitable means may be selected for heating the mould, including hot blocks, hot oil, radio frequency heating, hot air, infrared radiation or a laser source.

The advantage of the method of the present invention is that it provides an effective mounting of the stent onto the balloon/delivery system and also may permits the formation of pillows on the balloon where desired, which both aid stent retention on the balloon/delivery system and help guide the stent/delivery system into the guide catheter if the assembly is being retracted without deployment.

In a further aspect, the present invention also provides a heat set mould for use in a method for mounting a stent onto a balloon on a stent delivery system, the mould being split along its longitudinal axis to provide a top cavity portion and a bottom cavity portion which in use, are positioned together over the stent and stent delivery system assembly, with the top cavity portion and bottom cavity portion locked together so that the cavities provided in the portions to form the required finished profile for the delivery system assembly.

The mould may include at least one mould holder to facilitate clamping of the mould in a forming machine and also for clamping the mould sections together during the method of the invention.

The mould of the invention has the advantage that it is a relatively easy operation to position the stent/balloon assembly in the mould.

In a further aspect, the present invention provides a heat set apparatus which incorporates the heat set mould.

BRIEF DESCRIPTION OF THE DRAWINGS

The invention will now be described more particularly with reference to the accompanying drawings in which.

DETAILED DESCRIPTION OF THE INVENTION

Figure 3:
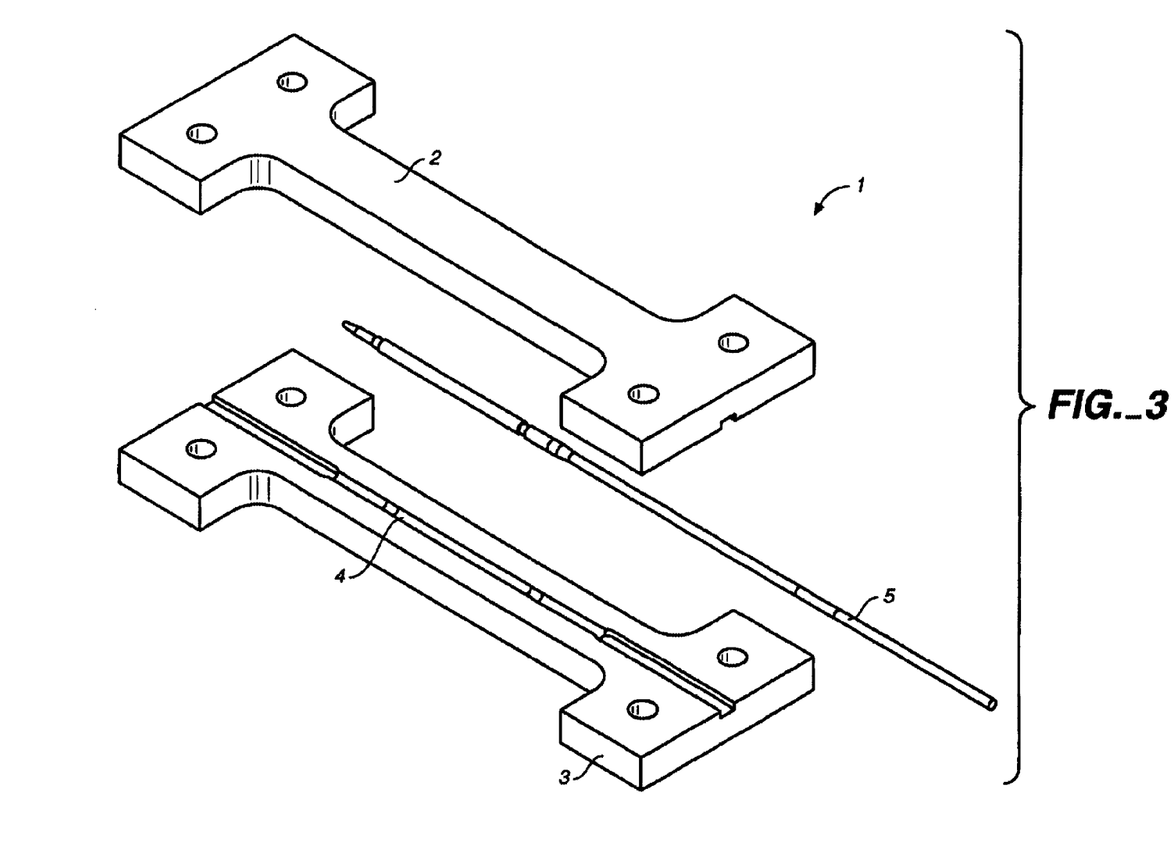
FIG. 3 is a perspective view of the mould of the present invention.
Figure 4:
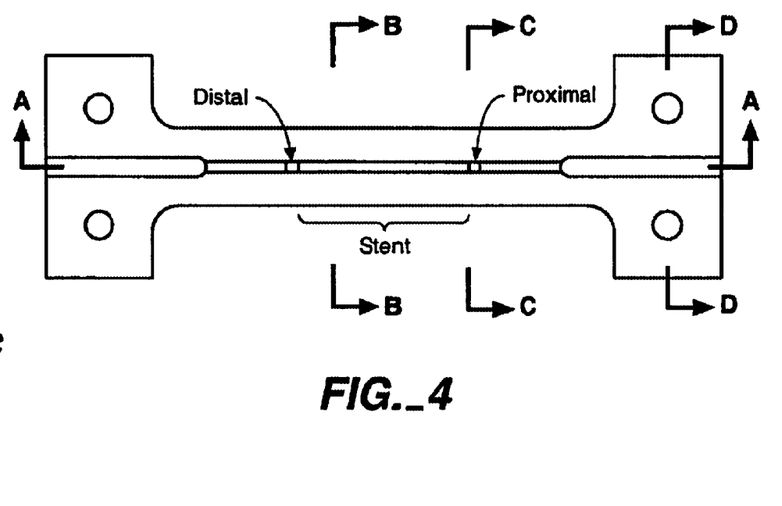
FIG. 4 is a plan view of the one half of the mould of the present invention.
Figure 4A:
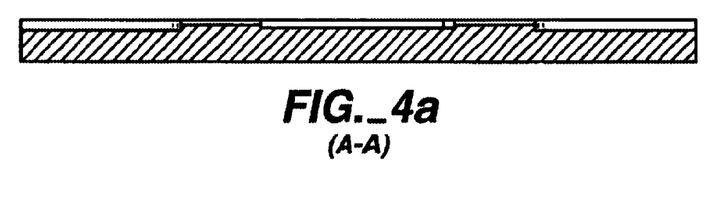
FIG. 4a is a cross-sectional view along the line A—A of FIG. 4.
Figure 4B:
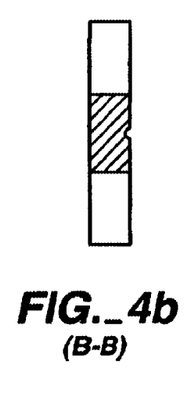
FIG. 4b is a cross-sectional view along the line B—B of FIG. 4.
Figure 4C:
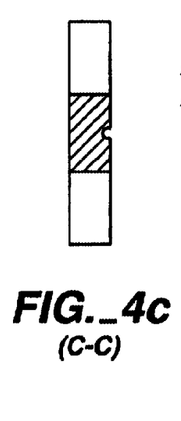
FIG. 4c is a cross-sectional view along the line C—C of FIG. 4.
Figure 4D:
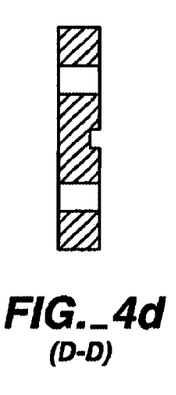
FIG. 4d is a cross-sectional view along the line D—D of FIG. 4.

Referring initially to FIG. 3 and FIG. 4, the mould of the invention is indicated generally by the reference numeral 1 and includes a top portion 2 and a bottom portion 3 provided by splitting the mould along its longitudinal axis. Both the top portion of the mould 2 and the bottom portion 3 of the mould include a cavity or channel 4 for receiving a stent/balloon assembly 5 therein. Channel 4 includes sections 4a and 4b for formation of proximal and distal pillows 27 and 29 respectively.

In use, a stent balloon assembly is placed in the mould between the top and bottom parties portions 2, 3, then pressurised air is introduced into the balloon interior from the luer-fitting end of the stent/balloon assembly (not shown) and the mould is heated preferably by hot blocks, but any suitable method, including but not limited to hot oil, radiofrequency heating, hot air, infrared or a laser source. Typically, the mould is closed or locked into the closed position pneumatically. Other closing or locking means including mechanical, electrical or hydraulic means may be used alternatively or additionally.

Figure 5:
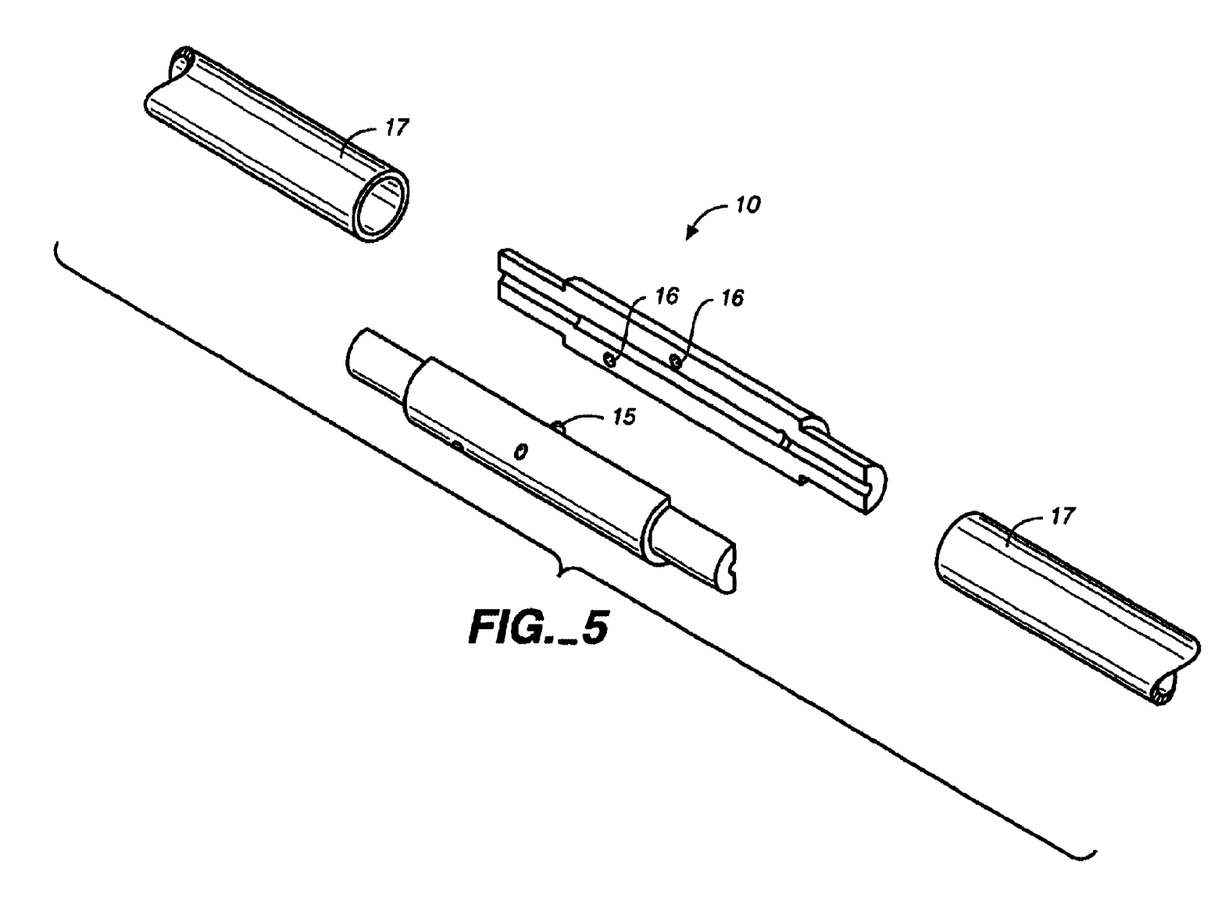
FIG. 5 is a perspective view of a second embodiment of the mould of the invention.
Figure 6:
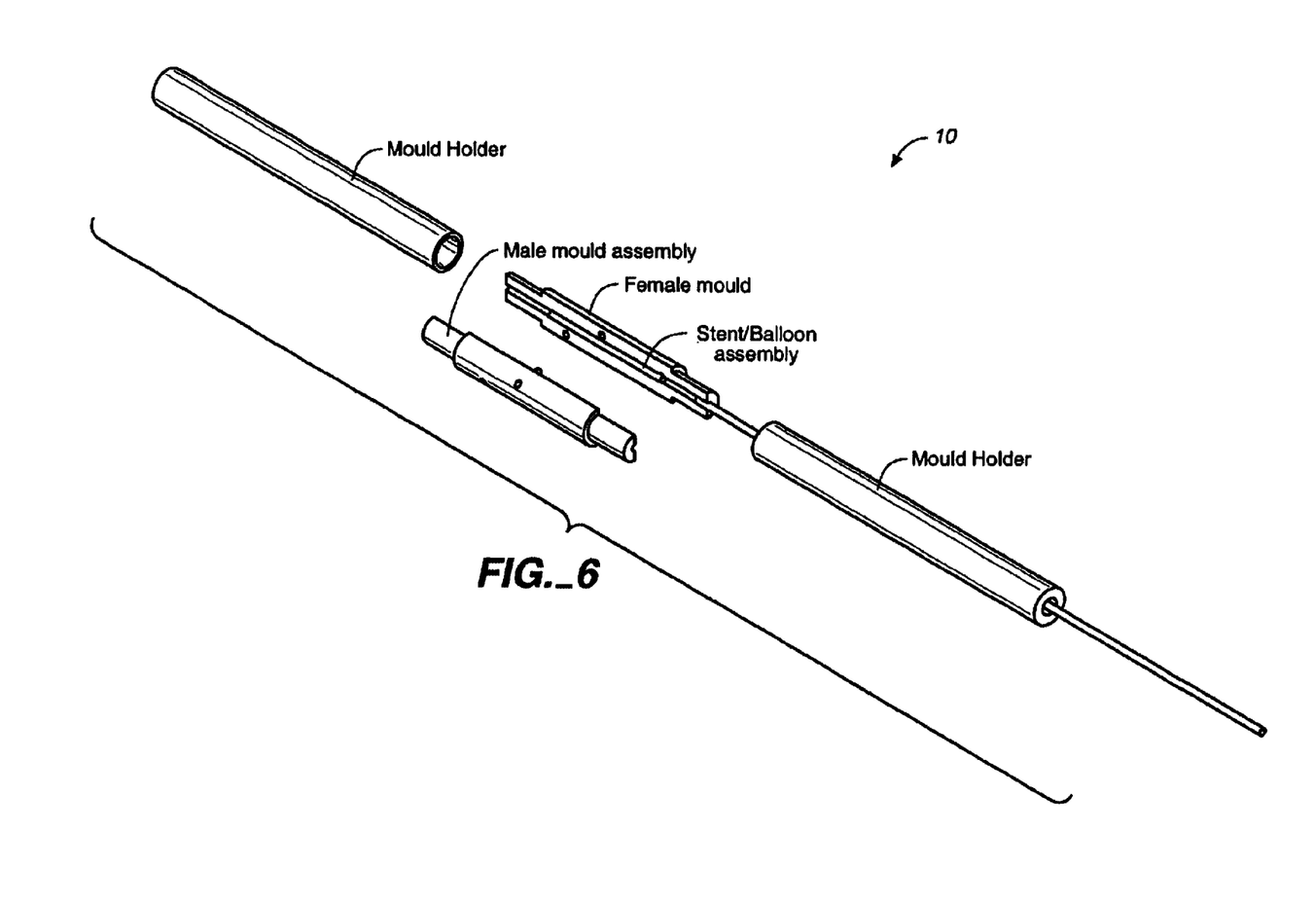
FIG. 6 is a perspective view of the second embodiment of the mould with the stent/balloon assembly shown positioned in the mould.

Referring to FIGS. 5 and 6, the mould in a second embodiment is indicated generally by reference numeral 10. The mould 10 is split longitudinally along its axis to provide a female mould section 12 and a male mould section 13. The male mould section 13 includes lugs 15 which engage into slots 16 in the female mould section 12 to interlock the two sections of the mould together once the stent/balloon assembly has been inserted in the female mould section as shown in FIG. 6.

FIG. 6 shows the heat set mould 10 of the second embodiment of the invention prior to its assemble about a balloon/stent assembly. The main parts of the mould required for the heat set operation are the male and female moulds 12 and 13. There are two mould holders 17 which facilitate clamping of the mould in the balloon forming machine and also clamping the mould together during the heat set operation. Alternatively, the function of the mould holders 17 could be incorporated in the heat set apparatus of the invention and not form part of the mould.

The temperature to which the mould is heated will depend on the materials being heat treated. Temperatures of about 93° C. are typical for use with stent/balloon assemblies for use in angioplasty, and temperatures up to 180° C. may be used if the characteristics of the material treated so demand or permit.

Likewise, the duration of the heating cycle will vary with requirements. Typical cycle times range between 2 minutes and 5 minutes. The cooling cycle which follows the heating cycle will likewise depend on the materials treated, coolant medium and coolant temperature. Either rapid or slow cooling may be employed, again depending on the materials being treated.

The advantages of the heat set mould and method of the present invention include the following. The heat set mould of the present invention allows more flexibility in the design of the final profile of the stent/balloon assembly to be achieved by splitting the mould along its longitudinal axis and providing cavities in the mould portion which are sized and shaped to give a desired final profile to the assembly. Examples of designs which can be manufactured using the mould and method of the invention are as follows:

Lower profiles: Currently the TFE sheaths need to have some clearance to allow them to be loaded axially over the stent. However, the mould of the present invention is split along its longitudinal axis so that the stent/balloon assembly does not need the same clearance in order to allow the mould to be positioned and hence it is possible to achieve lower profiles.

Tapered profiles: Again since the mould is split along its length it is possible to design in a tapered profile for the cavity or channel. This could be tapered from the proximal end to distal end or distal end to proximal end depending on the requirements as shown in FIG. 7b.

Selective profiling along the length: Again because of the mould design it is possible to selectively profile the stent along it's length during the heat set operation.

Figure 7A:
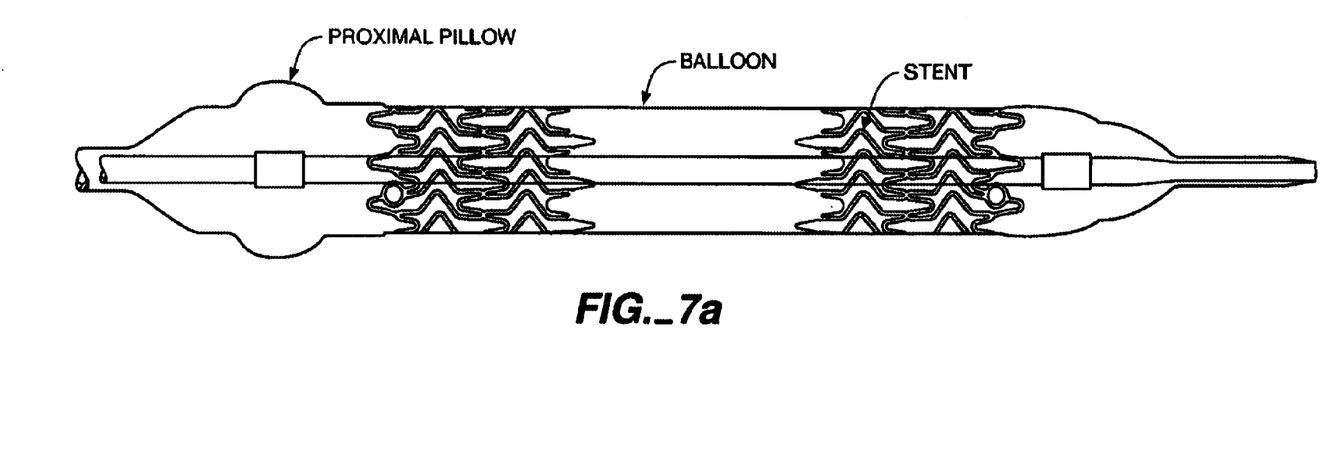
FIG. 7a is a sectional view showing a standard profile.
Figure 7B:
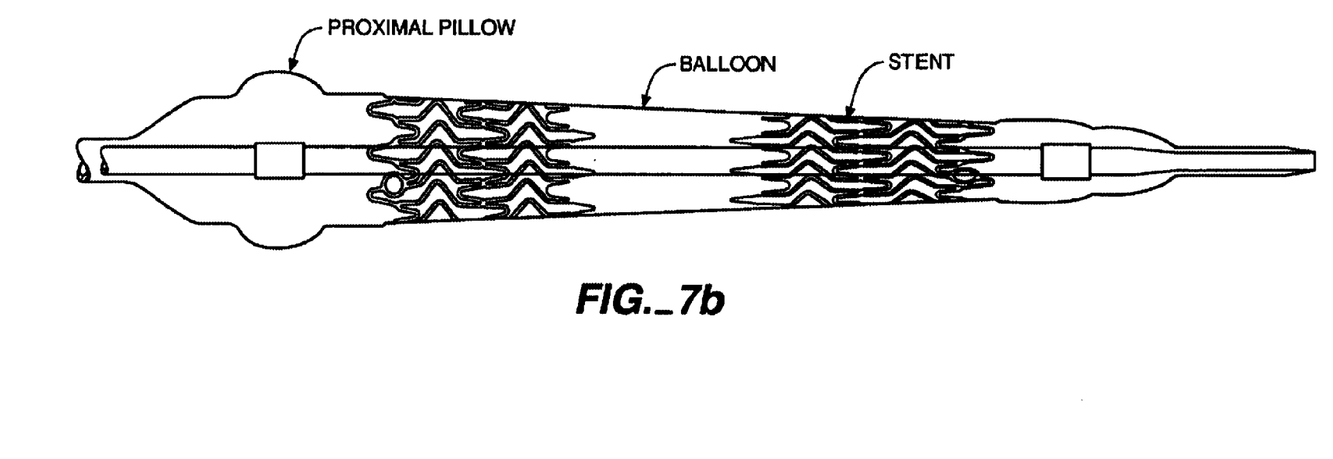
FIG. 7b is a sectional view along a tapered profile.
Figure 7C:
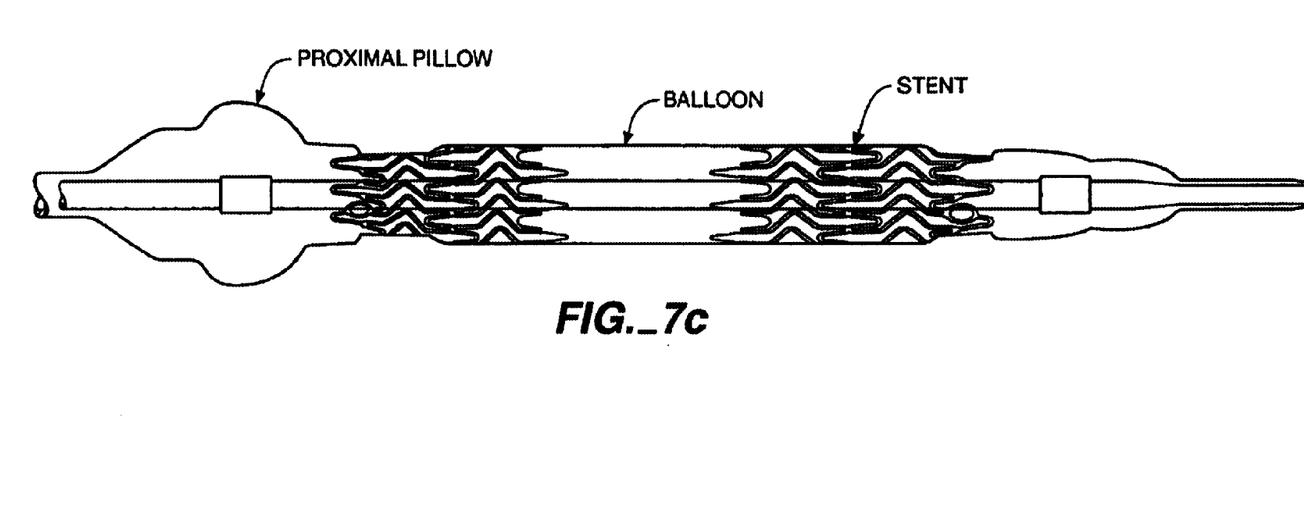
FIG. 7c is a sectional view of a reduced profile at proximal and distal ends.

FIG. 7a illustrates a delivery system with a standard stent profile; Stent 23 is positioned on balloon 24 with proximal balloon pillow 27 and distal balloon pillow 29, FIGS. 7b and 7c respectively show a stent 23 between proximal pillow 27 and distal pillow 29 on balloon 24 with a tapered profile and a profile reduced at both ends.

The method of the present invention is easier to automate than the process of the prior art. Positioning of the stent/balloon assembly in the mould of the present invention is an easier operation, better suited to automation than loading TFE sheaths onto the assembly and then heat mounting as in the prior art.

Use of the mould of the process of the invention eliminates the need for TFE sleeves to form the profile. This speeds up the process and also eliminates waste. The loading and correct positioning of the TFE sheathes is a very time consuming process. It is one of the slowest operations on the stent delivery system assembly line. Also the removal and discarding of sheaths after the heat set is wasteful. Those operations are eliminated by the use of the mould and method of the present invention.

It will of course be understood that the present invention is not limited to the specific details described above, which are given by way of example only, and that various modifications and alternations are possible without departing from the scope of the invention.

What is claimed is:

1. A mould apparatus for securing a stent onto a balloon of a stent delivery system, the stent delivery system balloon having a stent receiving portion intermediate a proximal balloon portion and a distal balloon portion, the stent mounted on the stent receiving portion, the mould apparatus comprising:

a mould body being split along its longitudinal axis to provide a top cavity portion and a bottom cavity portion which in use, are positioned together over the stent and stent delivery system with the top cavity portion and bottom cavity portion forming a finished profile for the delivery system the top and bottom cavity portions having a first section having a first diameter and a single second section with a second diameter, the second diameter smaller than the first diameter wherein the finished profile for the delivery system has a single stent section for receiving the stent mounted on the stent receiving portion and at least one balloon pillow section next to the single stent section for receiving the proximal balloon portion, the balloon pillow section having the first diameter and the stent section having the second diameter;

at least one mould holder to facilitate clamping of the mould cavity portions and;

a hot block coupled to the mould for providing heat to the first and second sections of the mould cavities.

2. An apparatus of claim 1 wherein the finished profile for the stent delivery system has a tapered profile.

3. An apparatus of claim 1 wherein the finished profile for the stent delivery system has a second balloon pillow section for receiving the distal balloon portion of the stent delivery system.

* * * * *